US 6,650,920 B2

(12) United States Patent
Schaldach et al.

(10) Patent No.: US 6,650,920 B2
(45) Date of Patent: Nov. 18, 2003

(54) APPARATUS FOR THE AUTOMATIC PERFORMANCE OF DIAGNOSTIC AND/OR THERAPEUTIC ACTIONS IN BODY CAVITES

(75) Inventors: Max Schaldach, Erlangen (DE); Curt Kranz, Berlin (DE); Jens Gobrecht, Gebenstorf (CH)

(73) Assignee: Biotronik Mess-und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 0 days.

(21) Appl. No.: 09/906,623

(22) Filed: Jul. 18, 2001

(65) Prior Publication Data

US 2002/0042570 A1 Apr. 11, 2002

(30) Foreign Application Priority Data

Jul. 18, 2000 (DE) .......................... 100 35 320
Aug. 18, 2000 (DE) .......................... 100 40 366

(51) Int. Cl.⁷ ................................. A61B 5/04
(52) U.S. Cl. ............... 600/374; 600/427; 600/439; 606/41; 606/194; 128/899
(58) Field of Search ............... 600/374, 424, 600/427, 439; 606/41, 194

(56) References Cited

U.S. PATENT DOCUMENTS

| 3,902,084 A | 8/1975 | May, Jr. |
| 4,154,242 A | 5/1979 | Termanini |
| 5,042,486 A | 8/1991 | Pfeiler et al. |
| 5,188,111 A | 2/1993 | Yates et al. |
| 5,386,741 A | 2/1995 | Rennex |
| 5,492,131 A | 2/1996 | Galel |
| 5,531,714 A | 7/1996 | Dahn et al. |
| 5,697,377 A | * 12/1997 | Wittkampf ............... 128/899 |
| 5,722,402 A | * 3/1998 | Swanson et al. ........... 600/374 |
| 5,899,860 A | * 5/1999 | Pfeiffer et al. ............ 600/424 |
| 5,906,578 A | * 5/1999 | Rajan et al. .............. 600/424 |
| 6,063,022 A | * 5/2000 | Ben-Haim ................. 600/41 |
| 6,095,150 A | * 8/2000 | Panescu et al. ........... 128/899 |
| 6,298,257 B1 | * 10/2001 | Hall et al. ................ 600/424 |
| 6,394,956 B1 | * 5/2002 | Chandrasekaran et al. .. 600/439 |

FOREIGN PATENT DOCUMENTS

| DE | 38 16 982 A1 | 12/1988 |
| DE | 43 06 136 A1 | 9/1994 |
| DE | 692 12 717 T2 | 3/1997 |
| DE | 691 27 538 T2 | 4/1998 |
| DE | 197 34 220 A1 | 2/1999 |
| DE | 199 09 066 A1 | 9/1999 |
| DE | 299 14 694 U1 | 2/2000 |
| EP | 0 518 205 B1 | 8/1996 |
| EP | 0 504 480 B1 | 9/1997 |
| WO | WO 96/31753 A2 | 10/1996 |
| WO | WO 97/44089 | 11/1997 |
| WO | WO 98/00060 A1 | 1/1998 |
| WO | WO 00/15286 A1 | 3/2000 |

* cited by examiner

Primary Examiner—Lee Cohen
(74) Attorney, Agent, or Firm—Browdy and Neimark, P.L.L.C.

(57) ABSTRACT

An apparatus for the automatic performance of diagnostic and/or therapeutic actions in body cavities is provided with a base control unit, which is to be arranged extracorporally, and with a catheter-type actuator, which is coupled therewith and which is insertable in the corresponding body cavity and which, in the vicinity of its distal end, is provided with a diagnostically active detection equipment and/or a therapeutically active treatment equipment, and which, at least in the vicinity of its distal end, is provided with an actuation mechanism, which is triggered by the base control unit, for advance and/or twist and turn control of the actuator.

27 Claims, 8 Drawing Sheets

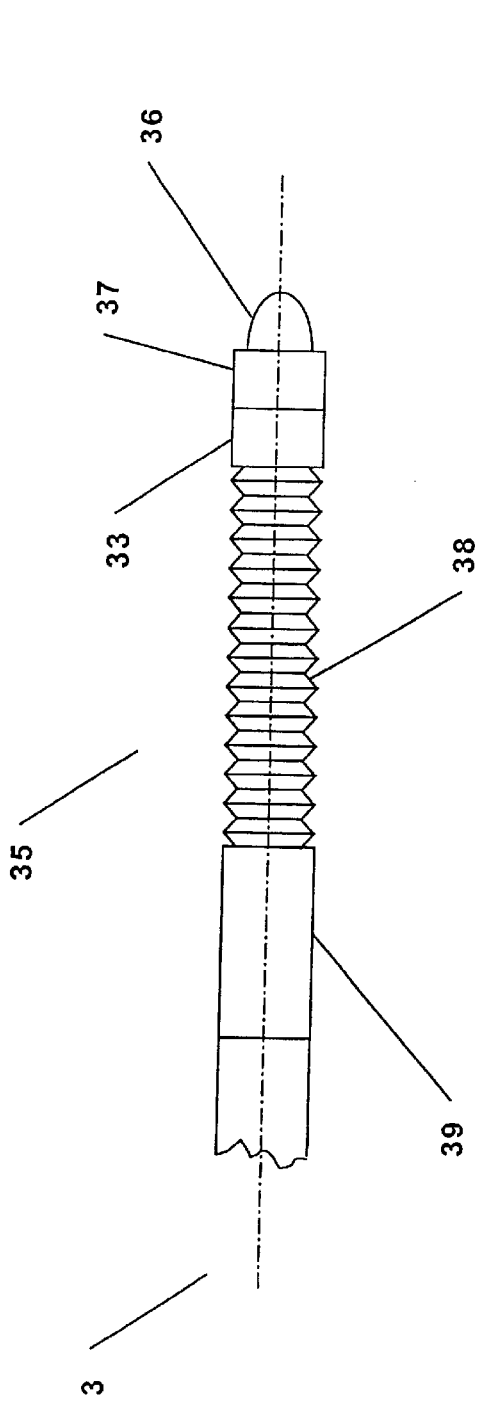
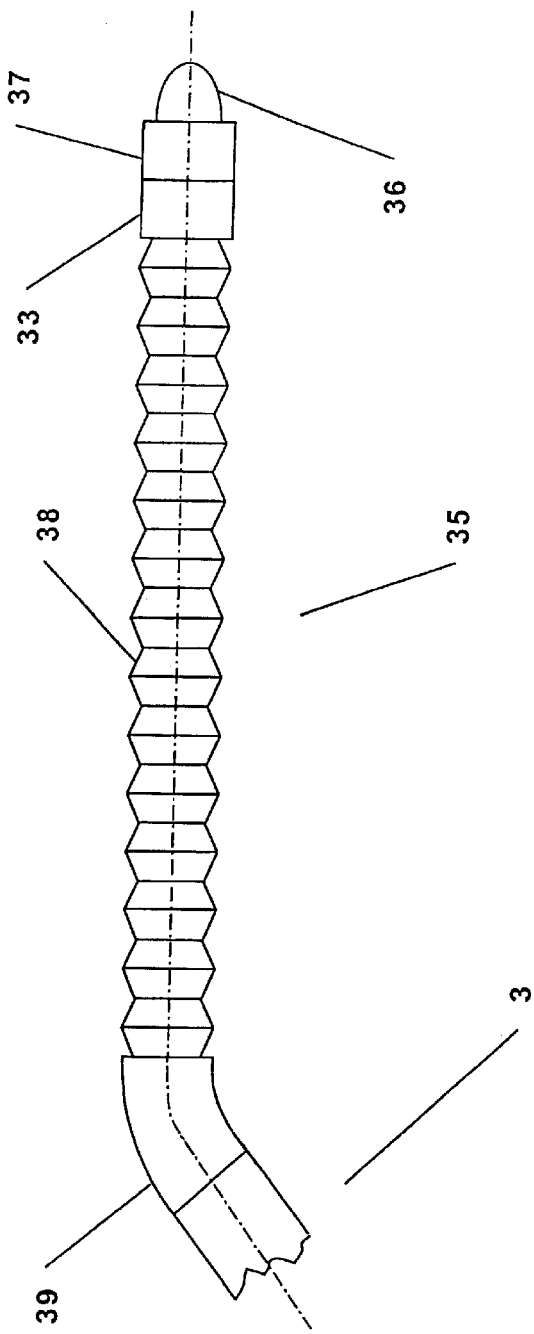
Fig. 4
Fig. 5

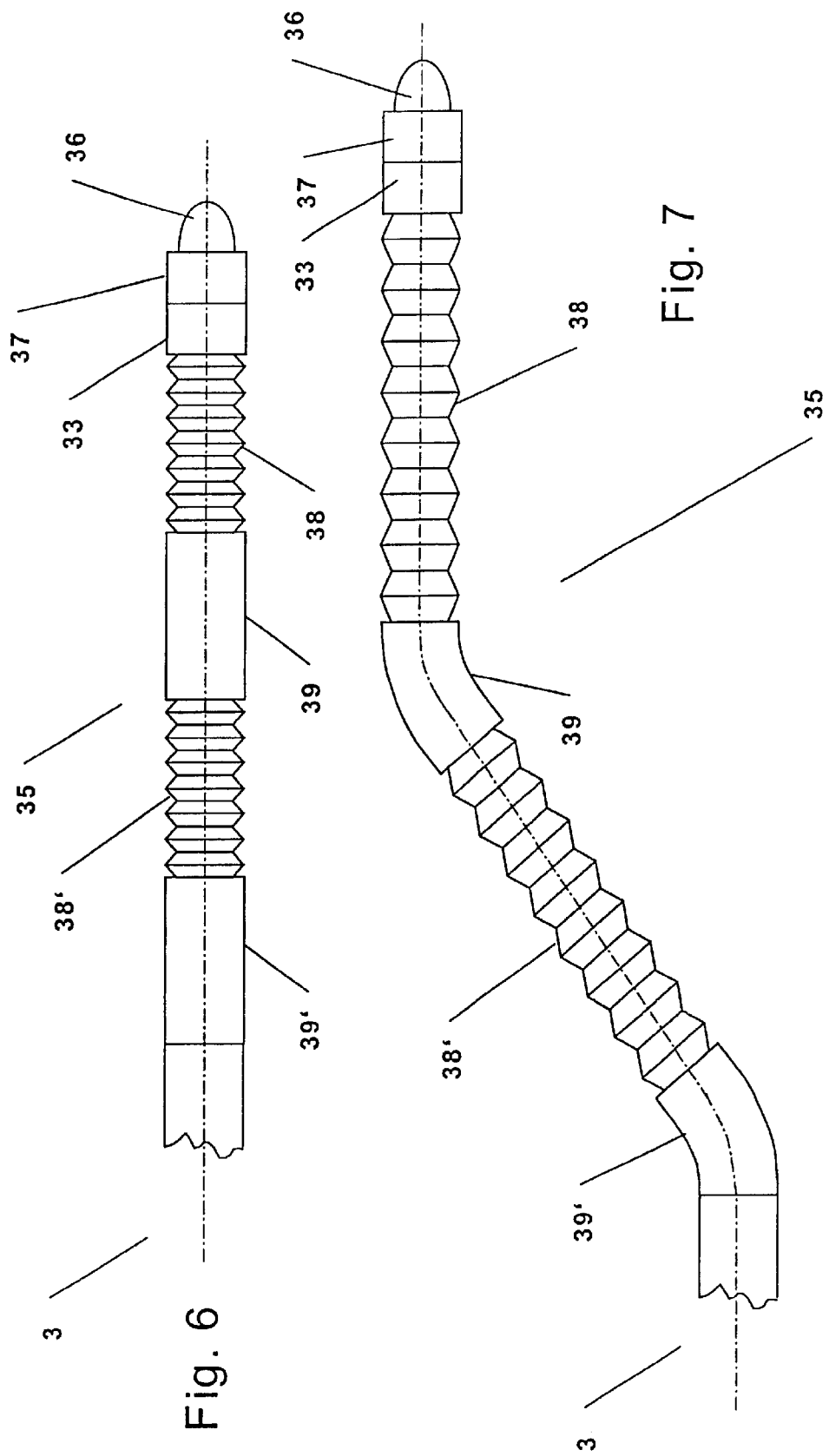

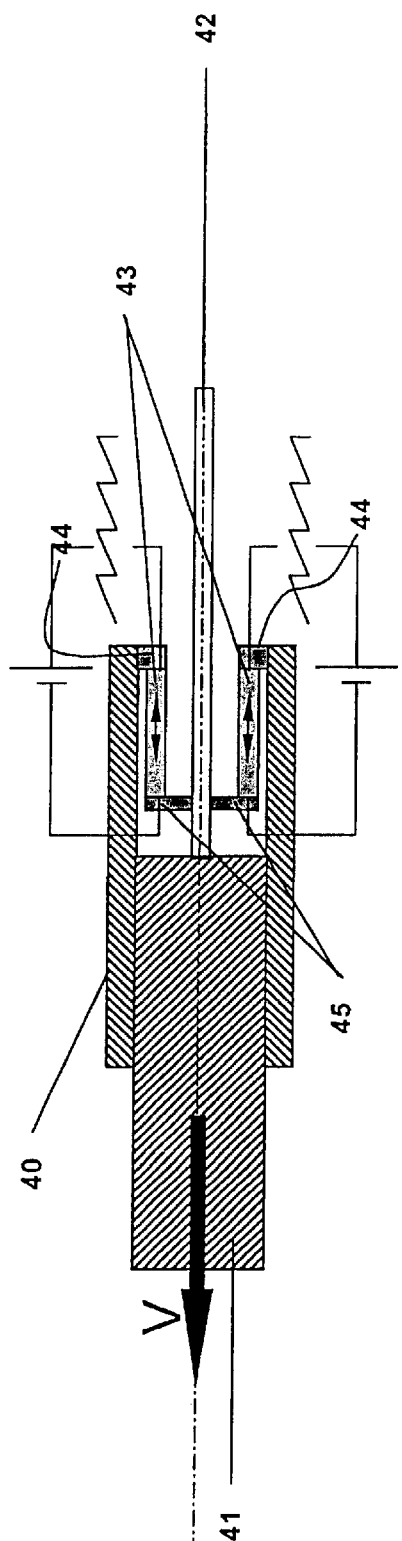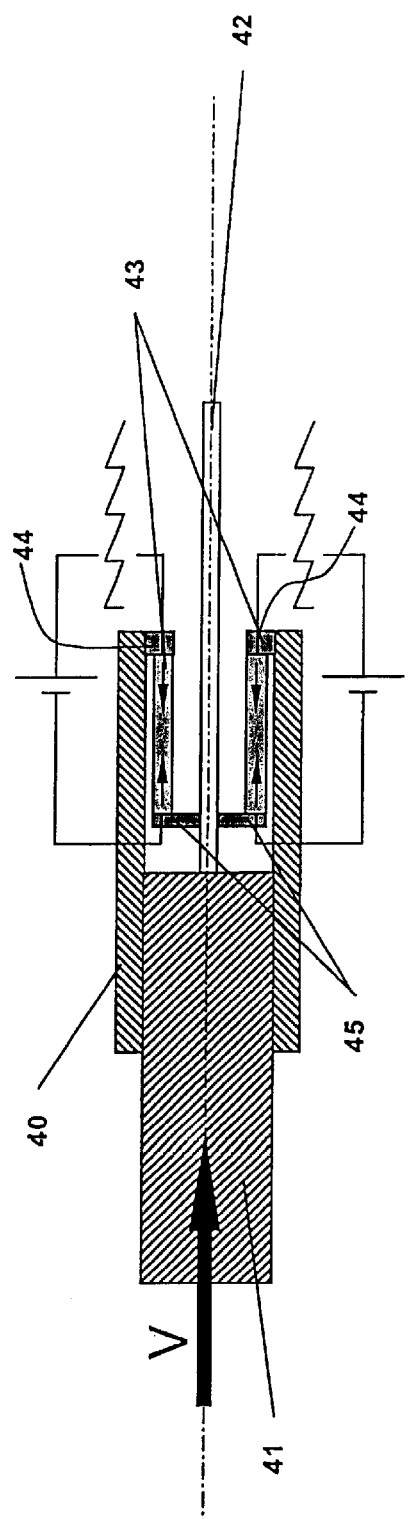

APPARATUS FOR THE AUTOMATIC PERFORMANCE OF DIAGNOSTIC AND/OR THERAPEUTIC ACTIONS IN BODY CAVITES

BACKGROUND OF THE INVENTION

1. Field of the Invention

The invention relates to an apparatus for the automatic performance of diagnostic and/or therapeutic actions in body cavities. Relevant instruments are catheters, cannulae, electrodes, endoscopes or the like, with body cavities meaning all kinds of organs and vessels to be examined in the human or animal body.

2. Background Art

A fundamental problem in these medical instruments resides in piloting them to the desired place of diagnosis or treatment within the cavity. Conventional mechanical steering devices are for instance rigid mandrels as a core or wire pulls in a catheter, it being possible, by a pull at these elements, to modify the twist and turn of the tip of a catheter, thus changing the direction of advance.

The prior art teaches various implements of the generic type, in which piezoelectric elements are used for control purposes. For example, U.S. Pat. No. 6,066,094 discloses a method and an apparatus of constructing a cardiac map of the heart, in which a steerable catheter is brought into contact with several locations in the heart where it is used to make measurements. U.S. Pat. No. 5,415,633 relates to an implantable instrument the distal end of which has sort of an annex that is controllable by means of piezoelectric elements.

U.S. Pat. No. 5,419,312 describes an endoscope coated with piezoelectric ceramic for controlling and steering purposes. This helps attain active pliability of the endoscope. A similar device is disclosed by U.S. Pat. No. 6,048,307. Finally, WO 97/22155 relates to a so-called piezoelectric motor working on the basis of an adjustable-length piezoelectric element.

SUMMARY OF THE INVENTION

It is an object of the invention to further develop a device of medical engineering of the type mentioned at the outset so that the actuator thereof is in a position largely automatically to move into contact with a single target or a plurality thereof, there taking corresponding diagnostic or therapeutic measures.

This object is attained by provision of a base control unit which is preferably extracorporal and with which is coupled an actuator of the type of a catheter that is insertable into the corresponding body cavity. In the vicinity of its distal end, the actuator is provided with a diagnostically active detection equipment or a therapeutically active treatment equipment, such as an ablation electrode, a dilatation balloon or the like. At least in the vicinity of its distal end and possibly over its full length—if necessary for reasons of maneuverability—the actuator is provided with an actuation mechanism for advance and/or twist and turn control that is triggered by the base control unit. Consequently, the base control unit may independently control the actuator and have him move into contact with certain locations, based on a corresponding control circuit or, in the way of a computerized numerical control system, based on a corresponding control program. Information about a surface contact of the distal end may be passed to the base control unit as input variables for the control system and may be used directly as a feedback variable in the control system. To this end, contact sensors are disposed preferably on the actuator's distal end, detecting any mechanical contact with the wall of the body cavity.

In keeping with further preferred embodiments, measuring sensors may be disposed on the actuator's distal end, detecting medically relevant data. These data may serve for diagnostic purposes, but they may also be used in the position control of the actuator. For instance, the instrument can localize pathological electric signals in the heart by measuring the potential on the myocardium. The instrument may spot locations that are to be treated by the actuator scanning the myocardium and by its measuring the corresponding potential signals.

Automatic placement in the vicinity of a stenosis is also conceivable to take place by means of impedance measurement in the vessel for the detection of blood stream and vessel volume.

Three-dimensional maps of coordinate plots of the cavity to be examined, which have been obtained by the aid of imaging techniques, may also serve as an alternative data base for the control of the actuator, in which case the respective location coordinates of the actuator are interrelated and corresponding control action is taken in accordance with the actuator's "schedule". Finally it also possible, alternatively or additionally, to place a so-called "navigation mark" as a point of reference in or in the proximity of the body cavity or even to arrange it extracorporally, this mark being detectable by corresponding sensors of the actuator. Based on this, signals may then be passed on to the base control unit, which are representative of the actuator's current position relative to the navigation mark. As actual actuation elements for the actuation mechanism of the actuator, the piezoelectric elements already mentioned, but also electrostrictive polymer elements (so-called "nanotubes") may be used as well as pneumatic or hydraulic actuation elements. Even the use of micro mechanic machine elements in nanotechnology is feasible, i.e. tiny gears, motors, transmissions etc.

Further preferred embodiments relate to special problems which occur distinctly during the application of the apparatus according to the invention in or on the heart. Being a pumping organ, the heart makes strong movements when it beats. Vessels next to the heart or the walls of the heart may easily collide comparatively vehemently with a catheter that has been inserted in the heart, which implies a certain risk of injury. Furthermore, keeping the precise position of treatment may be rather difficult or inaccurate because of the heartbeat. The consequences can be serious, in particular in the case of so-called ablations—i.e. sclerosing myocardial tissue for the suppression of pathological arrhythmias.

To avoid these problems, provision can be made for the actuator to track the motions of the body cavity which have been detected by suitable measuring or contact sensors, with the base control unit performing a corresponding feed and/or twist and turn control of the actuator. Further features, details and advantages of the invention will become apparent from the ensuing description of exemplary embodiments of the subject matter of the invention, taken in conjunction with the drawing.

BRIEF DESCRIPTION OF THE DRAWING

FIGS. 4 and 5 are lateral views of the distal end of an actuator in two different positions;

FIGS. 6 and 7 are analogous illustrations of an actuator in a second embodiment;

FIGS. 8 and 9 are diagrammatic sectional illustrations of a piezoelectric stick-and-slip feed element;

DESCRIPTION OF THE PREFERRED EMBODIMENTS

Figure 1:
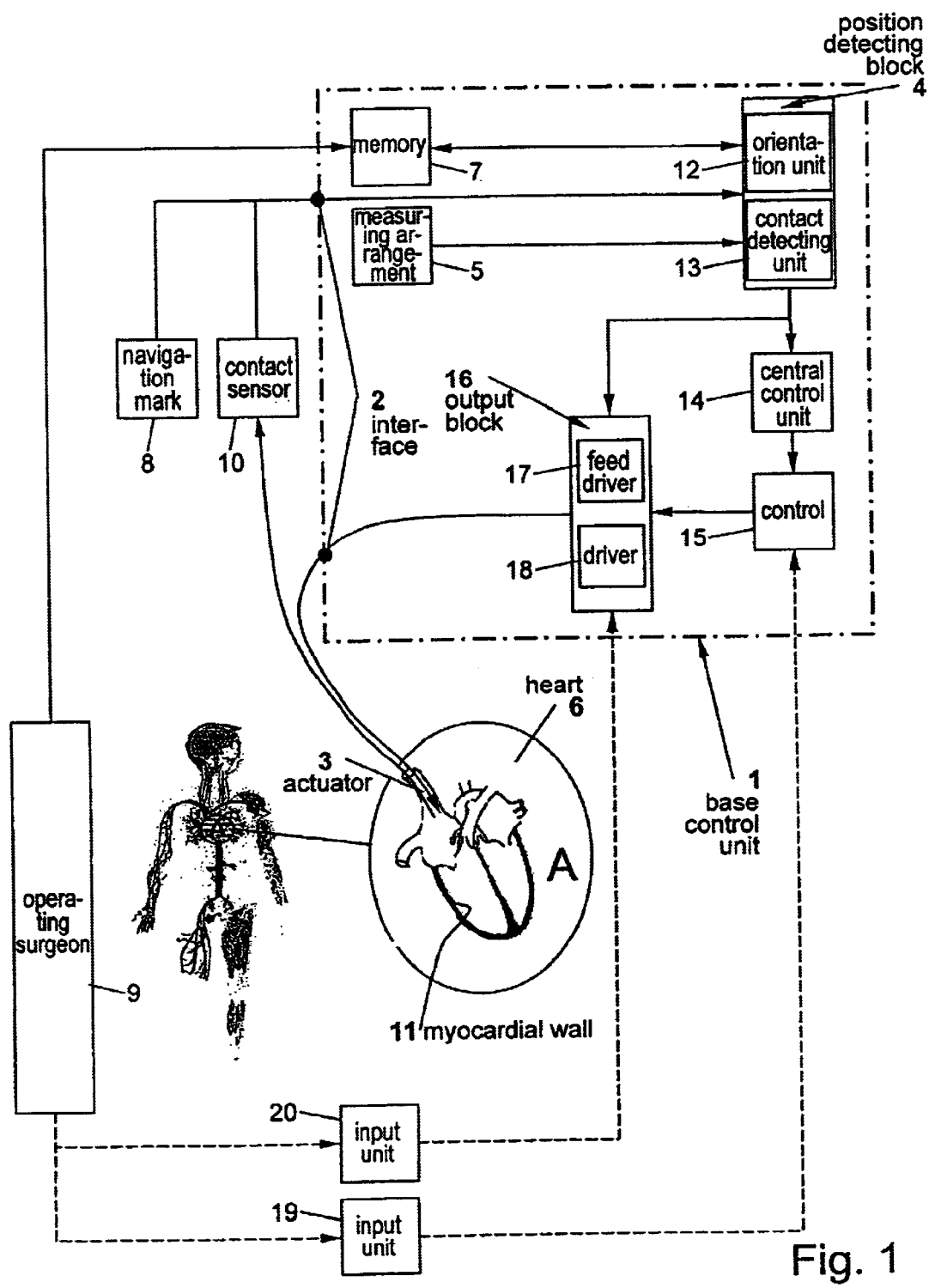
FIG. 1 is a diagrammatic block diagram of the entire apparatus.

The overall concept of an apparatus according to the invention for the automatic performance of medical actions in body cavities is explained, taken in conjunction with FIG. 1. Fundamentally, a base control unit is provided, which is designated in its entirety by 1 and which includes the components shown within the encircling dot-dashed line. This base control unit 1 is for instance a pc-based control unit having a corresponding interface 2 toward an actuator 3—a cardiac catheter in the present embodiment—which is coupled with the control unit. It stands for the most varying types of actuators such as endoscopes, electrodes or cannulae.

The base control unit 1 sub-divides into various functional regions, one of them being the position detecting block 4 which is substantially responsible for detecting the actual position of the actuator 3 on the basis of various input variables. Ranking among them is a measuring arrangement 5, by the aid of which a corresponding region of the body, such as the heart 5, is detected three-dimensionally by means of ultrasonography or X-radiation and corresponding coordinate data of the cardiac structures are determined. The corresponding data are recorded in a memory 7.

In a modified embodiment, the position and shape of the respective body cavity may be determined by means of imaging techniques (for example x-rays or ultrasonography) and any modifications in position and shape of the cavity produced by a patient's motions (heartbeat, respiration) may be measured. Since these motions are periodical, it is possible, in some cases, in advance to compute the position and shape of the body cavity under regard at any instant by the control unit without renewed strain on the patient by the imaging technique.

Furthermore, a navigation arrangement is allocated to the position detecting block 4, for instance in the form of a navigation mark 8, which is illustrated as a diagram block in FIG. 1, but is really placed for instance in the coronary sinus of the heart 6 or extracorporally by the operating surgeon 9. The navigation mark is linked via the mentioned interface 2. The coordinates of the actuator's tip relative to the navigation mark 8 may be determined by corresponding sensors (not shown in detail) on the actuator 3 and transmitted to the position detecting block 4.

Finally, the actuator 3 is provided with a contact sensor 10 (again illustrated as a diagram block) which detects any mechanical contact of the actuator 3 with for instance the myocardial wall 11 of the right ventricle and emits a corresponding signal via the interface 2 to the position detecting block 4.

Instead of a contact sensor 10, a probe may be employed, sensing the distance from a wall. It detects the distance between the actuator 3 and the wall of the heart. This is of interest for instance when the actuator carries a dilatation balloon. Another application resides in brachytherapy with the actuator 3 having to be seated centrally in the vessel.

Corresponding to the linkage of the measuring arrangement 5, navigation arrangement 8 and contact sensor 10, the position detecting block 4 comprises an orientation unit 12 and a contact detecting unit 13. The orientation unit 12 processes the coordinate data of the measuring arrangement 5 or of the corresponding data from the memory 7, interrelating them to the data made available by the navigation arrangement 8. Correspondingly, the contact detecting unit 13 processes and prepares the data furnished by the contact sensor 10.

A central control unit 14 serves for processing the data of the orientation unit 12 and contact detecting unit 13, computing a corresponding advance parameter control 15, namely for the length and direction of advance of the actuator 3.

By means of these data, the output block 16 is triggered, which comprises a feed driver 17 for triggering the corresponding actuation elements in the actuator 3 for the latter to be advanced and for twist and turn modification thereof. Furthermore, a driver 18 is provided for the treatment functions available in the actuator 3, such as an ablation electrode or a dilatation balloon.

If the operating surgeon 9 wishes to intervene manually in the apparatus sequence, input units 19, 20 are provided for access to the control and the output block 16.

Figure 2:
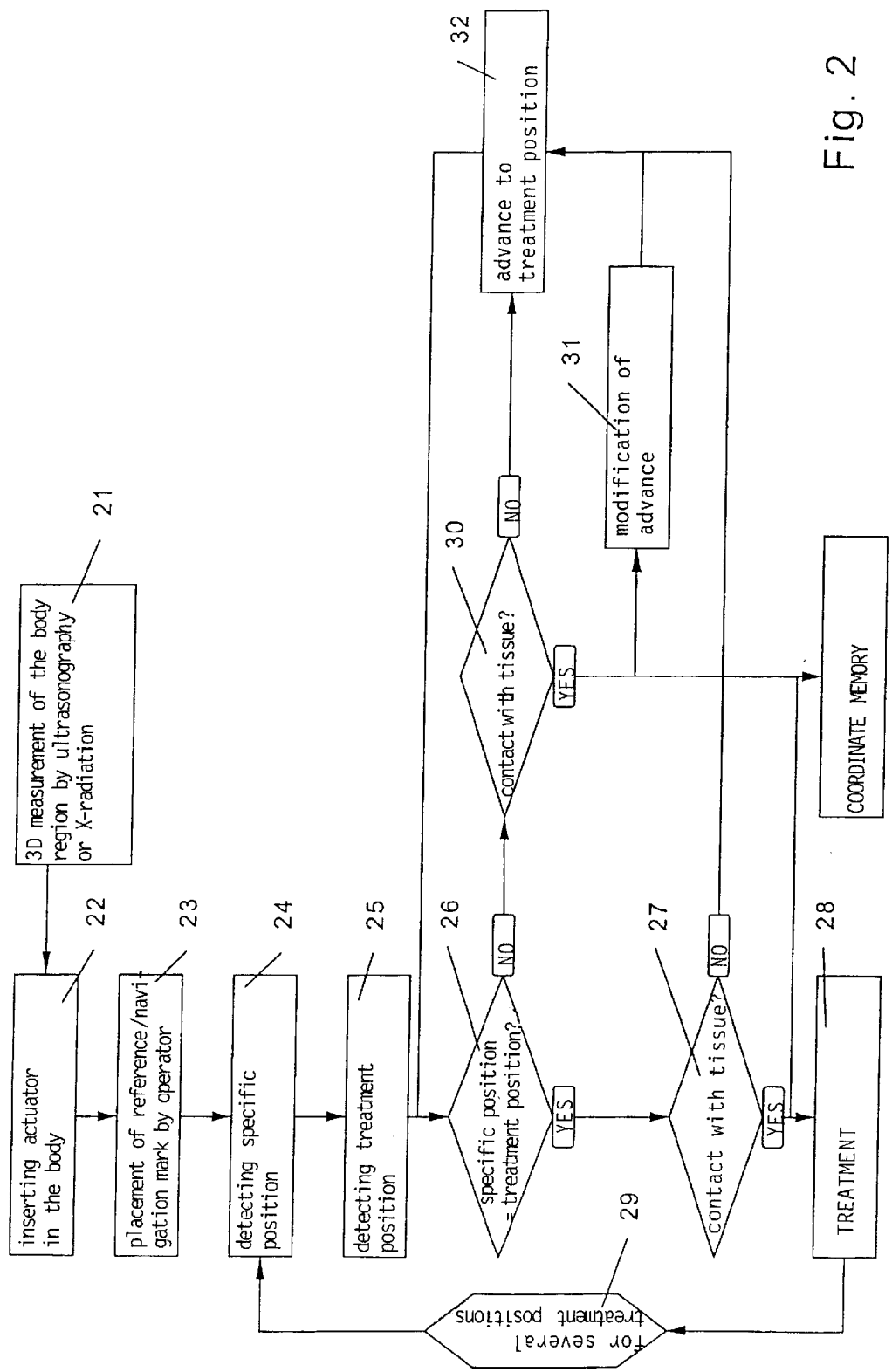
FIG. 2 is a flow chart of the control process within the control unit.

Use in practice of the diagnosis-and-therapy apparatus according to the invention is explained, taken in conjunction with the flow chart seen in FIG. 2. After three-dimensional measurement by ultrasonography or X-radiation (block 21) of the body region to be examined, the actuator is inserted in the body (block 22). This may take place by insertion of a catheter that represents the actuator into the right cardiac atrium. Then the navigation mark 8 is placed by the operating surgeon 9 for instance in the coronary sinus (block 23). Interrelating the distal end of the catheter, which is inserted in the heart, to this navigation mark 8 helps detect the position specific to the distal end of the catheter by the aid of the position detecting block 4 (block 24). By a corresponding input, the actual treatment position is determined and defined in the control unit 14. This enables detection of the treatment position to be the next step (block 25).

The ensuing inquiry in the program sequence determines whether the actuator's position corresponds to the treatment position. If so, an inquiry 27 is performed as to whether the distal end of the actuator 3 is in contact with tissue. If so, actual treatment may take place (block 28) for instance by activation of a ablation electrode for sclerosing or for removing cardiac tissue. If several treatments are to take place at varying positions, the process is returned to step 24 via the feedback 29.

If the inquiry 26 has found that the position of treatment has not yet been reached, another inquiry 30 determines whether the actuator is in contact with tissue. If so, a modification of feed (block 31) is effected by way of access to the coordinate memory 7 for the actuator to be advanced in accordance with the direction of the desired position of treatment (block 32). Starting from the inquiry 26, this loop of inquiries is kept on until the inquiry 26 finds that the actuator's position is identical with the position of treatment. In this connection it must be mentioned that constructing a map of the heart 6 is feasible not only by the imaging techniques mentioned at the outset, such as ultrasonography or X-radiation. By alternative or in addition, measurement of the heart may also take place by the aid of the contact sensor 10. As soon as it probes any contact with the myocardial wall, the corresponding coordinates can be read in the coordinate memory 7 so that corresponding scanning of the myocardial wall by the actuator 3 gives a topological image of the walls that define the respective body cavity.

Figure 3:
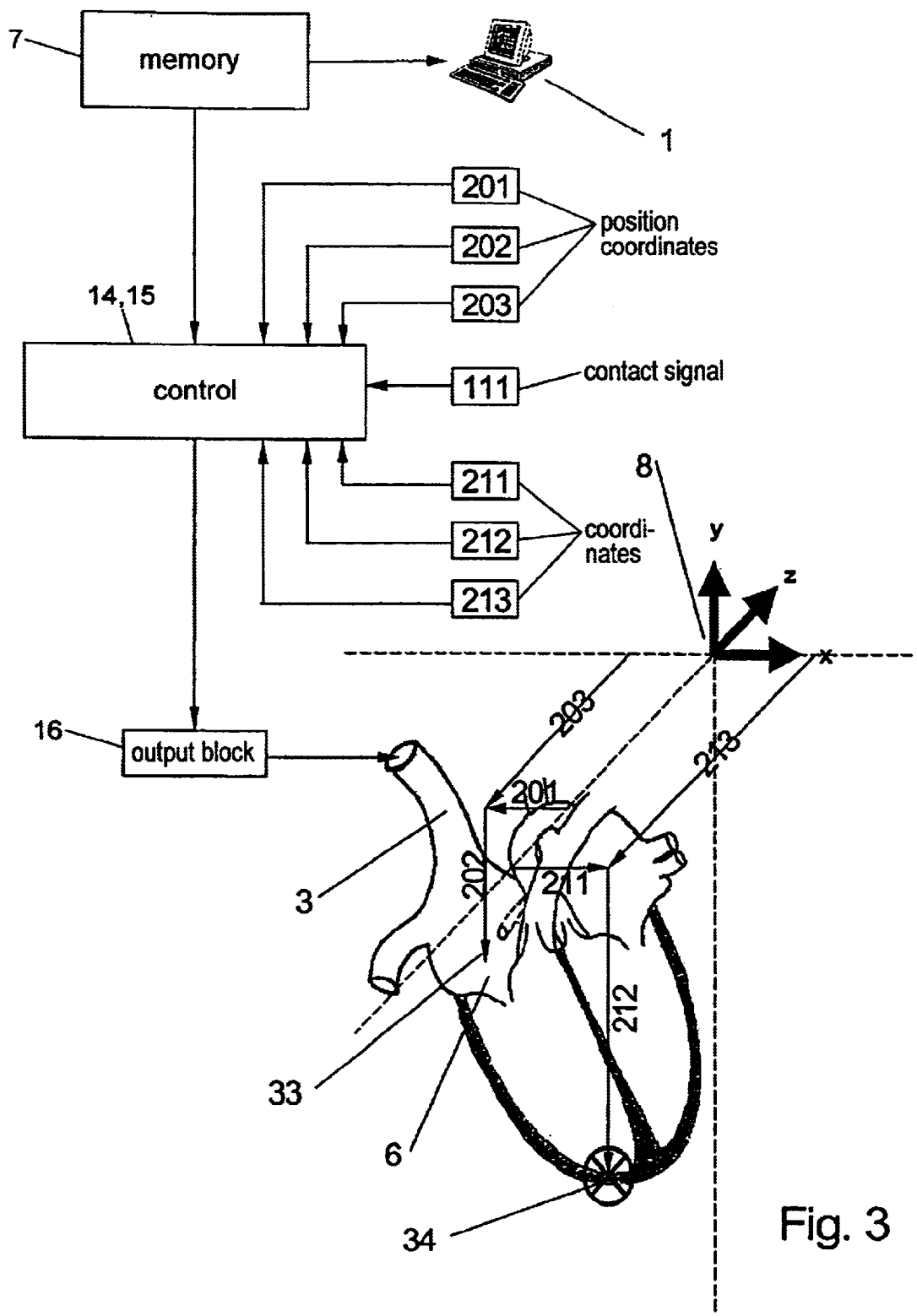
FIG. 3 is a diagram of the coordinate control of the apparatus.

The navigation routine of positioning the actuator 3 within the heart is explained on the basis of FIG. 3. In the vicinity of its distal end, the actuator 3 is provided with a position finding element 33, by the aid of which are determined the position coordinates 201, 202, 203 of the actuator 3 in relation to the navigation arrangement 8, which is represented by the system of coordinates x-y-z in FIG. 3. The treatment position 34 marked by a cross has the coordinates 211, 212, 213. Based on a comparison of the coordinates 201, 202, 203 on the one hand and 211, 212, 213 on the other, the control unit 14 and the control 15 determine the direction and length of the necessary advance of the actuator 3. This is accompanied with a contact signal 111, which is active when the distal end of the actuator 3 bears against a wall of the heart 6. Finally, the heart measurement coordinates recorded in the memory 7 of the base control unit 1 are used to determine the feed coordinates in order for any collision of the distal end on its way to the treatment position 34 to be precluded as far as possible.

The control data correspondingly found for the actuator 3 are fed to the output block 16 which implements the physical control of the actuator by activation of corresponding advance elements.

FIGS. 4 and 5 show the distal end 35 of an actuator 3. An ablation electrode 36 is roughly outlined directly at the end, by the aid of which corresponding therapeutic treatment of the heart can be effected. The ablation electrode 36 is followed by a contact sensor 37 in the form of a ring electrode. The adjoining ring represents the position finding element 33 of the actuator. This is followed by an adjustable-length element 38, which may be extended or retracted for instance by piezoelectric actuation as described below. As compared to FIG. 4, FIG. 5 shows the extended position of the adjustable-length element 38, which is outlined by the stretched out concertina folds.

The adjustable-length element 38 is followed by a pliable element 39 which, inside, comprises piezoelectric elements that are distributed over the circumference. Selectively triggering individual piezoelectric elements helps confer the pliable element from its stretched out condition into a bent condition (FIG. 5).

The version seen in FIGS. 6 and 7 differs from the version according to FIGS. 4 and 5 only in that two adjustable-length elements 38, 38' and two pliable elements 39, 39' are provided. Otherwise, reference can be made to the description in connection with FIGS. 4 and 5.

Attention is drawn to the fact that the mentioned piezoelectric elements or electrostrictive elements for modification in length and twist and turn may combine with mechanical wire pulls. For instance, the outer wall portions on one side of the actuator 3 may be stiffened by voltage being applied to the mentioned elements, while the flexible wall on the other side of the actuator 3 is bent by a wire pull. If the distal end is rotary about its axis, then the actuator may be advanced in virtually any direction. It is also conceivable to use several piezoelectric or electrostrictive elements and wire pulls to avoid rotatability.

Figure 10:
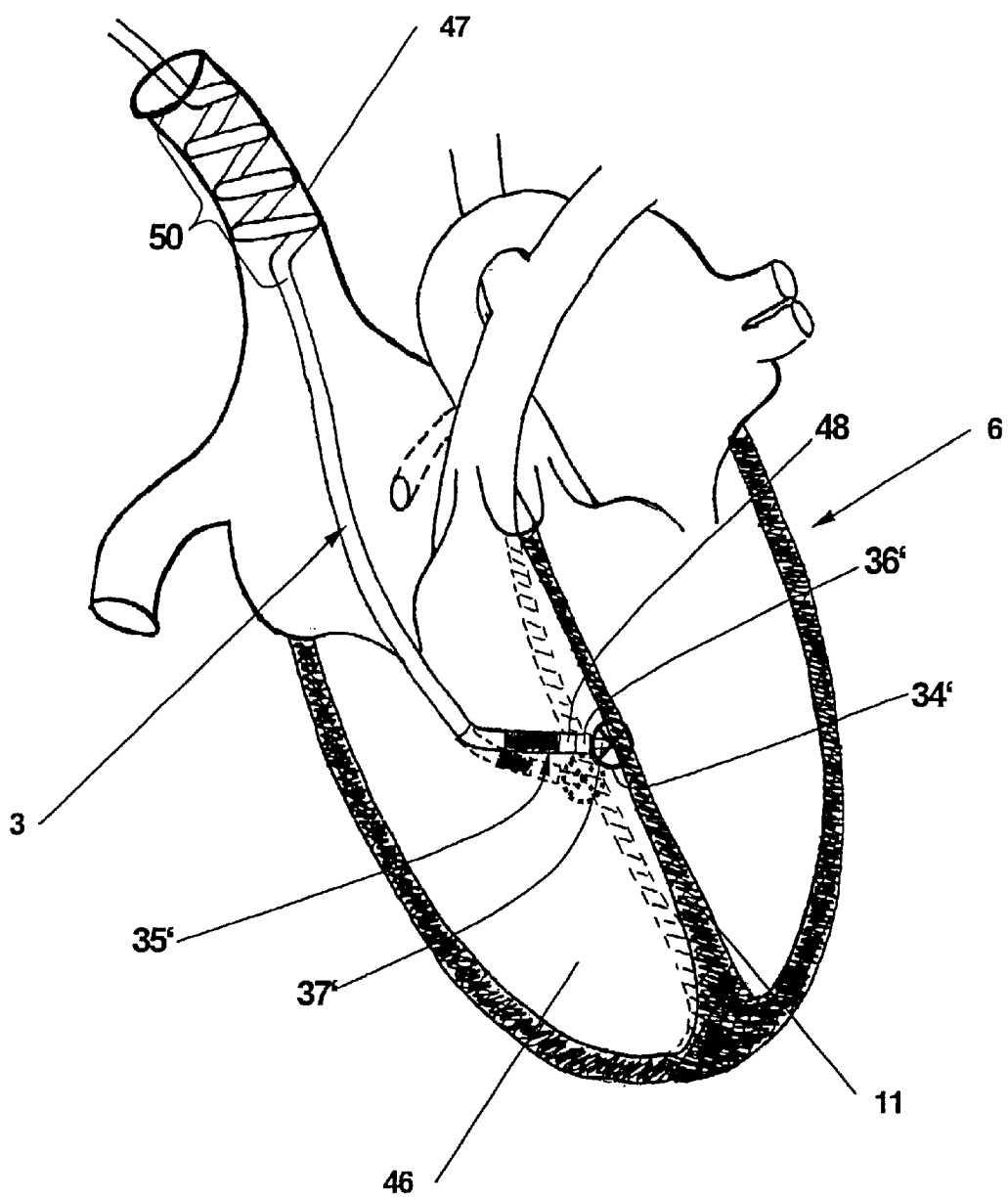
FIG. 10 is a diagram of the heart with an actuator led in that can track cardiac motion.

FIGS. 8 to 10 illustrate a micro mechanical, piezoelectric actuation element in the form of a so-called stick-and-slip actuation element. A slide 41, which is in contact for example with the distal end of the actuator 3, is seated for lengthwise displacement in an outer bearing sleeve 40. A slide element 42 is mounted on the inner end of the slide 41 in the longitudinal direction thereof. Positioned around the slide element 42 are piezoelectric elements 43, the rear end of which is tightly joined to the bearing sleeve 40 via an abutment 44. The free end of the piezoelectric elements 43 is provided with a contact projection 45, for example of a kind of neoprene material, which is in frictional engagement with the slide element 42. If the piezoelectric elements 43 are actuated by sawtooth voltage of flatly ascending and steeply descending flanks (FIG. 8), then lengthwise extension of the piezoelectric elements 43 is slow and lengthwise contraction is fast. As a result of the slow lengthwise extension, the slide element 42 is driven ("stick") and advanced in the feed direction V according to FIG. 8; in doing so, it is however not able to react to the rapid contraction in the opposite direction ("slip") so that the net result is a direction ("slip") so that the net result is a displacement of the slide element 42 and thus of the slide 41 in the feed direction V.

If the sawtooth voltage is reversed and applied with flanks steeply ascending and flatly descending, the contact projections 45 drive the slide element 42 in the feed direction V', whereas the slide element 42 is again not able to react upon rapid extension. The net result is a motion of the slide 41 in the feed direction V' according to FIG. 9.

FIG. 10 shows an actuator 3' in the form of an ablator in a position in which it is inserted in the right ventricle of the heart 6. In addition to the actual ablation electrode 36', the distal end 35' includes a measuring sensor 48, for instance in the form of an ultrasonic sensor, measuring the distance of the distal end 35' of the actuator 3' from the cardiac septum 11'. This helps detect the amplitude and frequency of the motion of the cardiac septum 11' and corresponding data are transmitted to the base control unit 1 (not shown in FIG. 10). On the basis of these data, the base control unit 1 computes corresponding control data for the distal end 35' of the actuator 3', which—as explained in detail above in connection with the actuator 3—is provided with corresponding actuation devices for the advance and twist and turn control of the actuator. Correspondingly, the actuator 3' may be moved uniformly toward the myocardial tissue that is in motion or to the desired position of treatment without any undesired collisions with the myocardial tissue.

For the accuracy of this process to be ensured, the actuator 3' has a spirally expandable medial section 50. Catheter sections of this type are known per se, serving for anchoring the actuator 3' for instance in the vena cava 47 as seen in FIG. 10.

Figure 11:
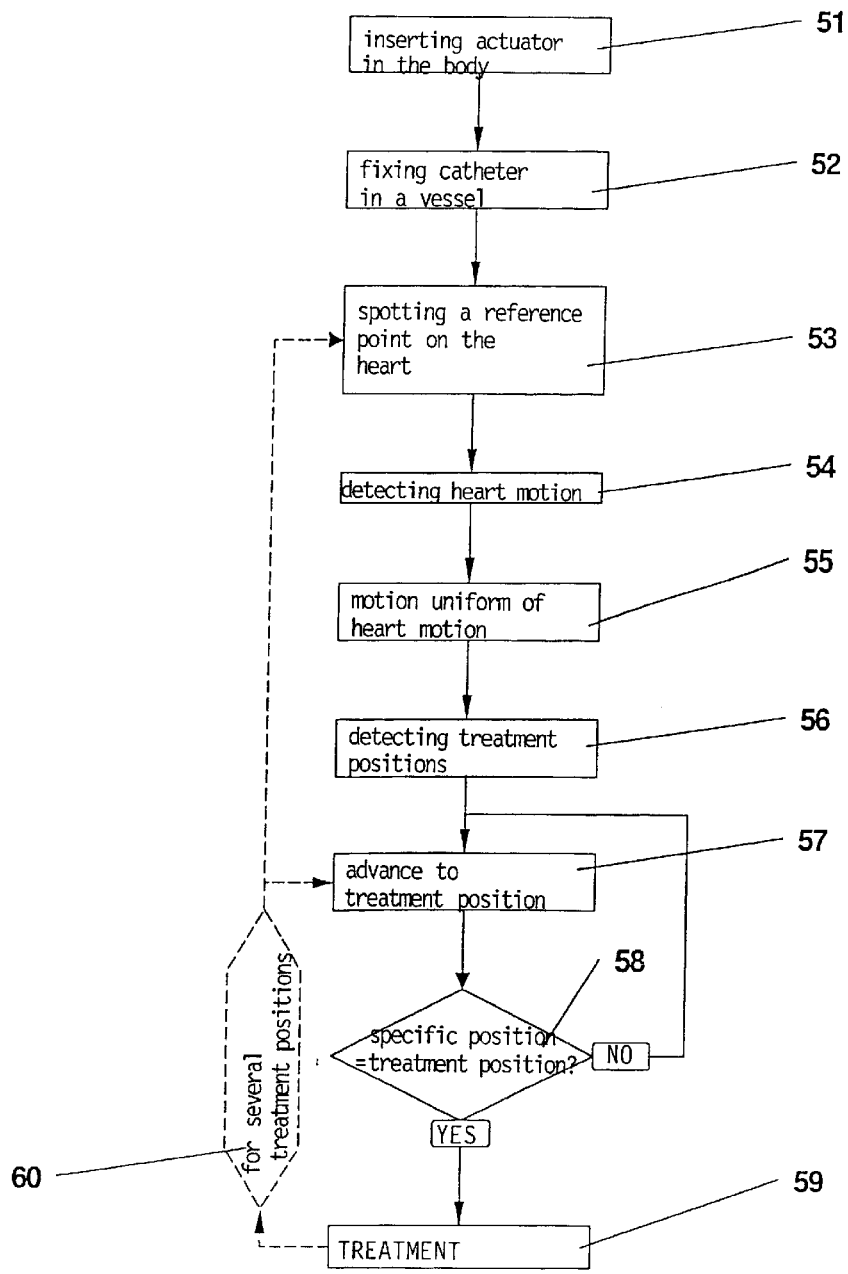
FIG. 11 is a flow chart of the control process within the control unit with the actuator tracking.

The following is an explanation of how to proceed during insertion and placement of the actuator 3' in the heart illustrated, taken in conjunction with FIG. 11.

In a step 51, the catheter-type actuator 3' is advanced via a vein as far as into the heart 6. A mandrel is inserted in the catheter so that the spiral medial section 50 is stretched out. Once the actuator 3' has reached its base position in the heart 6, the mandrel is removed from the actuator 3', which is thus fixed in the corresponding vessel 47 by the medial section 50 spiraling and expanding (step 52).

Instead of the conventional use of a mandrel for deformation control of the medial section 50, actuation devices may analogously be incorporated there in the form of piezoelectric elements, electrostrictive polymer elements, micro mechanical actuation elements or the like, which can be automatically triggered and thus activated by the base control unit. The deformation, correspondingly produced, of the medial section 50 helps fix the catheter-type actuator 3' in the vessel 47.

Thus inserted and fixed, the actuator's 3' distal end 35' projects freely into the heart 6. From this moment on, the actuator 3' is able to work substantially independently and without the help of an operating surgeon. Controlled by the base control unit 1, the actuator spots a reference point on the myocardium (step 53) and then detects the cardiac motion by way of the measuring sensor 48 (step 54). Via the corresponding actuation devices in its distal end, the actuator 3' is then controlled uniformly of the determined cardiac motion by the base control unit 1, which is roughly outlined by dashed lines in FIG. 10. While this step 55 is maintained, one or several treatment positions are then detected (step 56), for instance by pathological electric signals being spotted by suitable sensors. In this way, an ablation catheter can find required places of sclerosing. Further examples of control parameters for the localization of treatment positions are the flow rate for instance in the coronary cardiac vessels when a balloon catheter is to be controlled for the detection of the place that is to be dilated.

Then the actuator 3' is driven to the desired position of treatment 34' (step 57). This is accompanied with a regular inquiry 58 as to whether the actuator's position corresponds to the treatment position. This inquiry takes place by way of the navigation arrangement and the orientation unit of the apparatus as explained in detail in conjunction with FIG. 1. If the specific position does not correspond to the treatment position, the process returns cyclically to step 57.

Once the position of treatment is reached, actual treatment takes place in accordance with step 59. If several positions of treatment are to be localized, the process is returned by the feedback 60 either to step 57 or to step 53 as roughly outlined in FIG. 11 by short or long dashes.

What is claimed is:

1. An apparatus for automatically performing diagnostic or therapeutic actions in body cavities (6), comprising
    a base control unit (1); and
    a tubular actuator (3, 3') coupled to said base control unit,
        said tubular actuator having a distal end (35, 35') that is insertable into a corresponding body cavity (6), and
        which, in a vicinity of the distal end (35, 35') is provided with at least one of a diagnostically active detection equipment and a therapeutically active treatment equipment (36, 36'), and
        which, at least in a vicinity of the distal end (35, 35'), is provided with an internal actuation mechanism (43) triggered by the base control unit (1) via the actuator (3, 3') for at least one of advance control and twist and turn control of the actuator (3, 3'), wherein the internal actuation mechanism is selected from the group consisting of electromechanically operated advance elements, pneumatic actuation elements, hydraulic actuation elements and piezoelectric stick-and-slip actuation elements,
            wherein the actuator (3') has an expandable medial section (50) for it to be anchored in a body cavity (6).

2. An apparatus according to claim 1, wherein the distal end (35) of the actuator (3) is provided with a measuring sensor for detection of medically relevant data, as a diagnostically active detector.

3. An apparatus according to claim 1, wherein the distal end of the actuator (3, 3') is provided with at least one of an ablation electrode (36, 36') and a dilatation balloon as a therapeutically active treatment equipment.

4. An apparatus according to claim 1, wherein the actuator (3, 3') is provided with a contact sensor (10, 37, 37') for detection of mechanical contact with the wall (11, 49) of the body cavity (6).

5. An apparatus according to claim 1, wherein the base control unit (1) includes an orientation unit (12) for advance and direction control of the actuator (3, 3'), with a coordinate plot, detected by measurement, of the corresponding body cavity (6) being recorded in a memory (7) as a basis for actuator control.

6. An apparatus according to claim 5, further comprising means for measuring the coordinates recorded in the memory (7) by imaging techniques.

7. An apparatus according to claim 5, further comprising a contact sensor (10, 37, 37') for measuring the coordinates recorded in the memory (7).

8. An apparatus according to claim 7, wherein motions of the body cavity (6) that are to be measured are detected by the contact sensor (10, 37) and incorporated in the measurement.

9. An apparatus according to claim 1, further comprising reference navigation means (8) connected to the base control unit (1) to be placed in, or in proximity to, the body cavity, functioning as a point of reference for determination of a position of the actuator (3).

10. An apparatus according to claim 1, further comprising at least one of a measuring and contact sensor (48) incorporated in at least one of an advance control and a twist-and-turn control of the actuator (3) for the distal end (35') of the actuator (3') to detect any motions of the body cavity (6) and track the motions of the body cavity (6).

11. An apparatus according to claim 1, wherein the medial section (50) is expandable spirally or by waves for anchoring in a blood vessel (47).

12. An apparatus according to claim 1, wherein deformation of the medial section (50) of the actuator (3') is produced by an automatically controllable actuation mechanism.

13. An apparatus for automatically performing diagnostic or therapeutic actions in body cavities (6), comprising
    a base control unit (1); and
    a tubular actuator (3, 3') coupled to said base control unit,
        said tubular actuator having a distal end (35, 35') and being insertable into a corresponding body cavity (6), and
        which, in a vicinity of the distal end (35, 35') is provided with at least one of a diagnostically active detection equipment and a therapeutically active treatment equipment (36, 36'), and
        which, at least in a vicinity of the distal end (35, 35'), is provided with an internal actuation mechanism (43) triggered by the base control unit (1) via the actuator (3, 3') for at least one of advance control and twist and turn control of the actuator (3, 3'),
            wherein the actuator (3') has an expandable medial section (50) for it to be anchored in a body cavity (6).

14. An apparatus according to claim 13, wherein the distal end (35) of the actuator (3) is provided with a measuring sensor for detection of medically relevant data, as a diagnostically active detector.

15. An apparatus according to claim 13, wherein the distal end of the actuator (3, 3') is provided with at least one of an ablation electrode (36, 36') and a dilatation balloon as a therapeutically active treatment equipment.

16. An apparatus according to claim 13, wherein the actuator (3, 3') is provided with a contact sensor (10, 37, 37')

for detection of mechanical contact with the wall (11, 49) of the body cavity (6).

17. An apparatus according to claim 13, wherein said internal actuation mechanism comprises advance elements for electromechanical operation, said advance elements comprising at least one of piezoelectric elements, electrostrictive polymer elements and micro mechanical actuation elements.

18. An apparatus according to claim 13, wherein an actuation mechanism for the actuator (3, 3') is formed by at least one of pneumatic and hydraulic actuation elements.

19. An apparatus according to claim 13, wherein the base control unit (1) includes an orientation unit (12) for advance and direction control of the actuator (3, 3'), with a coordinate plot, detected by measurement, of the corresponding body cavity (6) being recorded in a memory (7) as a basis for actuator control.

20. An apparatus according to claim 19, comprising imaging means for detecting the coordinates recorded in the memory (7).

21. An apparatus according to claim 19, further comprising a contact sensor for detecting the coordinates recorded in the memory (7).

22. An apparatus according to claim 21, wherein motions of the body cavity (6) that are to be measured are detected by the contact sensor (10, 37) and incorporated in the measurement.

23. An apparatus according to claim 13, further comprising reference navigation means (8) connected to the base control unit (1) to be placed in, or in proximity to, the body cavity, functioning as a point of reference for determination of a position of the actuator (3).

24. An apparatus according to claim 13, wherein an actuation mechanism for the actuator (3, 3') is formed by piezoelectric stick-and-slip actuation elements (42, 43, 44, 45).

25. An apparatus according to claim 13, wherein any motions of the body cavity (6) are detected by at least one of a measuring and contact sensor (48) and are incorporated in at least one of an advance control and a twist-and-turn control of the actuator (3) for the distal end (35') of the actuator (3') to track the motions of the body cavity (6).

26. An apparatus according to claim 13, wherein the medial section (50) is expandable spirally or by waves for anchoring in a blood vessel (47).

27. An apparatus according to claim 13, wherein deformation of the medial section (50) of the actuator (3') is produced by an automatically controllable actuation mechanism.

\* \* \* \* \*